United States Patent [19]

Islam

[11] 4,346,118
[45] Aug. 24, 1982

[54] ANTIMICROBIAL AGENTS ADDED TO ANIMAL FEEDS

[75] Inventor: Mir N. Islam, Newark, Del.

[73] Assignee: University of Delaware, Newark, Del.

[21] Appl. No.: 146,322

[22] Filed: May 2, 1980

[51] Int. Cl.$^3$ ................................................. A23L 3/34
[52] U.S. Cl. ..................................... 426/335; 424/313; 426/532; 252/407
[58] Field of Search ......................... 424/313; 426/335

[56] References Cited

U.S. PATENT DOCUMENTS 2,218,181 10/1940 Searle et al. ......................... 424/313

OTHER PUBLICATIONS

McGowan et al., Ann. Applied Biol., vol. 35, (1948), pp. 25-36.
Grove, Ann. Applied Biol., vol. 35, (1948), pp. 37-44.

*Primary Examiner*—Bernard Helfin

[57] ABSTRACT

The invention relates to the preservation of all organic materials that are susceptible to biodeterioration.

Microbial growth, particularly of fungi, in food, feed, agricultural crops, manufactured goods, and cosmetic and pharmaceutical preparations are inhibited by the use of di-alkyl esters of fumaric acid and compositions thereof.

1 Claim, No Drawings

ANTIMICROBIAL AGENTS ADDED TO ANIMAL FEEDS

The present invention relates to agricultural and manufactured commodities that are spoiled or impaired because of the growth of microorganisms. More particularly, the invention is concerned with such compositions and methods which use antifungal agents for preservation of food, feed, and other organic materials that are susceptible to microbial attack.

BACKGROUND OF THE INVENTION

Microorganisms, particularly fungi including mold and yeast, are widespread in nature and their growth is facilitated by moderate temperature and high humidity. They cause heavy loss in stored seeds of all kinds. Cereal grains, oilseeds and tubers comprise the main foods and feeds of the world today. Following harvest these agricultural commodities are stored in bulk for some time before they are processed for food or feed. The processed material is often stored in bulk as well. Various molds such as Aspergillus, Penicillium and Rhizopus invade both the stored seed and the products made from it, and thus cause heavy losses. Estimates of the extent of loss for cereal grains range from 0.5–10% of the world's production. A solution to this problem would certainly have a major impact on the world food shortage.

Apart from the damage caused to cereal grains there is a considerable health hazard from fungal attack of food and feedstuff. Certain molds under appropriate conditions of temperature and humidity would produce mycotoxins of which the best known example is aflatoxin which is produced by *Aspergillus flavus*. Aflatoxin growing on peanuts, wheat and various cereal has been shown to cause illness to domesticated animals. It produces hepatic cancer in several species including rats and trouts. Also it has been implicated with liver cirrhosis in children. Aflatoxin is a major problem to the poultry industry because of its growth retarding effect on the young birds.

Among the products made from cereal grains bread and cakes are most commonly spoiled by mold. The main species involved in the spoilage of bakery products are *Rhizopus nigricans, Penicillium expansum, Aspergillus niger*, and *Monilia sitophila*. Practically all commercial flours are infected by mold to a certain degree. These molds, however, are killed during baking; but as soon as the freshly baked product comes out of the oven fungus spores fall on it and subsequently multiply. In addition to molds, there is also the problem of ropiness in bread because of certain species of Bacillus. According to a survey by the baking industry, the U.S. consumers loose several million dollars a year from spoiled bread.

The fungal problems with cereal grains, flour and baked products is very serious in the tropical countries. They contribute to malnutrition and many health hazards in the developing world. In the industrialized nations, fungal problems in stored feed often result in major economic losses. Several additives such as propionic acid and propionates, caprylic acid, acetic acid, dehydroacetic acid, benzoic acid and benzoates, monochloracetic acid, sorbic acid and sorbates have been suggested to prevent fungal attack of cereal grains, feedstuff, and bakery products. However, so far only the propionates have been used to any great extent. One major disadvantage with propionates, sorbates, and the benzoates is that their antimicrobial activity is dependent upon acidic pH (Sauer, F. "Food Technology," 31, pp 66–67, 1977) while most food and feed materials are at about neutral pH. Acidification of food or feedstuffs to optimize the effectiveness of these additives make the products unplatable, whereas at neutral pH the amount of additive requirement is substantially increased. Ultraviolet light has been used to prevent fungal comtamination with limited success. Recent interests for alternate means of preventing fungal contamination is evidenced by U.S. Pat. Nos. 3,934,045; 3,971,855; 4,083,999; and 4,123,552.

There are other food products that are susceptible to mold spoilage. These include fresh fruits and vegetables, dairy products, margarine and intermediate moisture products such as meat patties, smoked meat and fish, pet foods, cheese, dry fruits, jams, etc. The genera mainly responsible for the spoilage of vegetables and fruits include Fusarium, Rhizopus and Alternaria. Several chemicals have been suggested to control fungal spoilage of fruits and vegetables. These include zinc carbonate. crotonic acid, esters of vanillic or parabenzoic acid and biphenyl. For intermediate moisture products, the preferred additives are sorbic acid or potassium sorbate. There have been however many attempts to improve these methods as evidenced by recent U.S. Pat. No. 4,048,342. Sometimes for products like cheese, wrappers are impregnated with antimycotic chemicals such as benzoate, methyl and propyl parabens, caprylic acid, o-phenylphenol and dimethylolurea.

There are many non-food products which are also susceptible to mold. All wood is subject to fungal decay whether it is in the form of boats, beer barrels, bridges or bungalows. The so-called dry rot and wet rot of woods are caused by *Serpula lacrymans* and *Coniophora cerebella* respectively. The preservative often used for treating wood is creosote. Agricultural plants such as canes and chestnuts that are used in making furniture or fiber board are also susceptible to fungal attack. The result of such attack is a reduction in the quality of the plant material and the possibility of it being useless. Recently in U.S. Pat. No. 3,928,620, a combination of propionic acid and hydrocarbon mineral oil has been suggested to protect such material from microbial attack.

Other non-food products that are decayed by mold include leather goods, fabrics and canvas materials, twines and sandbags, books and bookbinders, paints, gums and glue, electrical insulation, rubber linings and conveying belts. There are also many cosmetics and drug preparations that require preservation from fungal attack. Typical examples would be skin creams, lipstick compositions and toothpaste. Several chemicals are incorporated or sprayed upon in order to preserve these products. The list of chemicals include o-phenylphenol, biphenyl, methyl paraben and propyl paraben. These and similar chemicals are also used as disinfectant spray to control machinery mold in industrial installations and to prevent mold and mildew in house-hold operations.

Living tissues of plants as well as of animals including human are susceptible to fungal attack. Plant diseases caused by fungi are multitudinous. The Irish potato famine of 1845–49 was caused by the species *Phytophythora infestans* which destroys foliage of the potato plant and also rots the tubers during storage. 'Blue mold' of tobacco is caused by the fungus *Peronospora tobacina* which destroys the leaves or, if the disease is not severe, reduces quality of the crop. 'Coffee rust' is caused by the fungus *Hemileia vastatrix* which attacks the foliage of coffee trees, causing the leaves to become desiccated and to fall prematurely. The resulting effect is a very poor coffee crop. Although coffee is not a major food crop the effect of *H. vastatrix* can be devastating on the economy of many countries that are heavily dependent on coffee.

The majority of human fungal diseases are caused by dermatophytes or 'ringworm fungi' which attack keratin-rich tissues namely the skin and hair. Most dermatophytes belong to two closely-related genera, Microsporum and Trichophyton. 'Ringworm of the scalp' particularly in children, is caused by two species of Microsporum. 'Athlete's foot' an infection that is familiar to most people is caused by *Trichophyton mentagrophytes* or *T. rubrum*. The warm and humid conditions of the feet facilitate fungal attack, particularly in the webs between the toes. The medicines used against ringworm and athlete's foot are griseofulvin and preparations containing Zinc undecylenate, Undecylenic acid, ortho-chloromercuriphenol, benzoic acid, solicylic acid, propyl paraben, etc.

The present applicant recognized the widespread detrimental effects of microorganisms as described above through personal and professional experiences and devoted considerable time to develop antimicrobial agents through screening of large numbers of chemicals.

OBJECTS OF THE INVENTION

Accordingly, the object of the invention is to provide a method of treating food, feed, agricultural crops and manufactured goods, and for hygienic purposes and the general care of human beings with a view to eliminating the detrimental effects of microorganisms, particularly fungi.

Following are more specific objects of this invention:

(a) to provide a method of treating cereal grains, oilseeds and animal feeds so that they can be stored for an extended period without spoilage;

(b) to provide a method which will inhibit the growth of aflatoxin producting mold, *Aspergillus flavus* in stored food or feedstuff;

(c) to provide a method which will extend the shelf-life of bakery products;

(d) to provide a method of preventing fungal attack of intermediate moisture food such as pet foods, dry fruits, etc.;

(e) to provide a method which will prevent fungi growth on fresh fruits and vegetables, and agricultural plants such as cane and lumber;

(f) to provide a method to prevent fungal attack of manufactured goods such as leather articles, canvas materials, twines, books, paints, rubber articles, etc.;

(g) to provide a method to control mold and mildew growth in household or industrial operations;

(h) to provide a method of preventing fungal attack of cosmetic and drug preparations; or (i) to provide a method of controlling fungal diseases of plants and animals including humans.

Other objects and advantages of the present invention will be apparent from the detailed description of the invention that follows.

DESCRIPTION OF THE INVENTION

The present invention is based on the discovery that di-alkyl esters of fumaric acid possess surprisingly strong antimicrobial activity. Fumaric acid is currently used as an acidulant (for tartness) in gelatin products such as Jello. However, no commercial use of its di-alkyl ester is known at present. Heretofore, the di-alkyl esters of fumaric acid have not been recognized as antimicrobial agents. Following is the general formula of di-alkyl esters of fumaric acid:

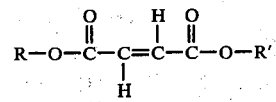

Di-alkyl ester of fumaric acid

The alkyl groups, i.e. R and R' can be methyl ($-CH_3$), ethyl ($-CH_2CH_3$), or propyl ($-CH_2CH_2CH_3$) depending on the degree of antimicrobial property desired. The preferred form, however, is the dimethyl ester which is known as dimethyl fumarate (DMF). Dimethyl fumarate exhibits antimicrobial activity far superior to those of propionic acid, propionates, sorbic acid, sorbates, benzoic acid and the benzoates. In addition it was discovered that the antimicrobial activity of the di-alkyl esters of fumaric acid is not dependent on pH as is the case with these antimicrobial agents. This is a distinct advantage of the di-alkyl esters of fumaric acid over the pH-dependent antimicrobial agents for use in food, feed, cosmetic or pharmaceutical systems.

It was also discovered that the di-alkyl esters of fumaric acid possess a broad spectrum activity against the growth of various microorganisms including fungi and bacteria. Growth of fungi belonging to the following genera/species were completely inhibited in pure culture systems by incorporating DMF at such low levels as 0.001–0.01% in potato dextrose agar (Difco) medium.

| | | | |
|---|---|---|---|
| 1. | Absidia | 13. | Geotrichum candidum |
| 2. | Alternaria citri | 14. | Hansenula anomala |
| 3. | Aspergillus flavus | 15. | Hansenula wengei |
| 4. | Aspergillus niger | 16. | Penicillium digitatum |
| 5. | Aspergillus oryzae | 17. | Penicillium expansum |
| 6. | Candida krusei | 18. | Penicillium roqueforti |
| 7. | Candida lipolytica | 19. | Rhizopus nigricans |
| 8. | Candida zeylanoids | 20. | Rhizopus oligosporus |
| 9. | Cladosporium | 21. | Rhizopus stolinifer |
| 10. | Cryptococcus albiens | 22. | Sporobolomyces |
| 11. | Debaryomyces kloeckeri | 23. | Thamnidium elgans |
| 12. | Fusarium | 24. | Torulopsis spaerica |

In addition, DMF was found to inhibit the growth of the following bacteria at levels ranging from 0.001–0.01% in tryptic soy broth (Difco):

| | | | |
|---|---|---|---|
| 1. | Alcaligenes viscolactis | 7. | Micrococcus flavus |
| 2. | Bacillus coagulans | 8. | Micrococcus lutea |
| 3. | Escherichia coli | 9. | Pseudomonas fluorescens |
| 4. | Lactobacillus acidophilus | 10. | Salmonella typhimuriun |
| 5. | Lactobacillus casei | 11. | Staphylococcus aureus |
| 6. | Lactobacillus plantarum | 12. | Vibrio parahemolyticus |

In view of the widespectrum antimicrobial property as demonstrated above and other experiments carried out, it is possible to prevent microbial deterioration of food, feed, agricultural crops and manufactured goods including cosmetic and pharmaceutical preparations by adding microbicidal amounts of the dialkyl esters of fumaric acid.

The terms "food" and "feed" used in this invention refer to any natural and processed or otherwise modified organic material which is susceptible to biodeterioration and which can be consumed by human beings, animals, birds and fish for nourishment. Examples would range from freshly harvested grains to pelletized feed.

The term "agricultural crops" in the present invention is intended to include any substance grown from the soil or from artificial nitrients, either in the form as collected or after alteration in form, such as grinding or pressing into a flour, paste, etc. The term is also meant to include cereal grains, legumes, oilseeds, nutseeds, dried fruits, tubers and root crops. Additional agricultural crops include silage, green wood (lumber), wood chip, wood pulp, canes; forage crops, flower bulbs; crop byproducts such as citrus pulp, apple pomace, almond hulls, etc.

The di-alkyl esters of fumaric acid are also useful in inhibiting fungus growth in organic materials of animal or aquatic origin such as leathers, wool, fishmeal, algae.

The di-alkyl esters of fumaric acid may also be employed to prevent fungal attack on manufactured commodities such as fabrics and canvas materials, twines and sandbags, books and bookbinders, paints, gums and glue, electrical insulation, rubber materials, conveying belts, cosmetics and drug preparations.

Besides the above uses, the di-alkyl esters of fumaric acid may be formulated into sanitizing products such as lysol spray to prevent mold and mildew growth in household and commercial operations. Also, the di-alkyl esters of fumaric acid may be incorporated in preparations to prevent or control fungal diseases of plants and animals including human.

The concentrations at which the di-alkyl esters of fumaric acid are applied to prevent fungus and mold growth depend upon the type of organic material being treated, its moisture content, the temperature and humidity and the period over which the preservation is desired. The higher these parameters the greater would be the need for fungicide. For most applications the amounts of di-alkyl esters of fumaric acid ranging from 0.0005 to 10% by weight of the material being treated are satisfactory.

Depending upon the material being treated, the di-alkyl esters of fumaric acid can be added directly thereto and mixed, or it may be added by using any substance as a carrier. For materials that are processed into a product, such as flour into bread, they can be incorporated as ingredients.

The following examples illustrate the invention and are not considered restrictive of the invention as otherwise described herein. Examples 1 and 2 compare the use of DMF with calcium propionate.

EXAMPLE 1

Dimethyl fumarate or calcium propionate at a level of 0.3% by weight is applied to several cereal grains and a legume (identified in Table 1) using talc as carrier. Four ventilated plastic containers are filled with each product for each treatment and then held at 72° F.±2° F. at a relative humidity of 80–82%. For comparison four containers of untreated products are also incubated under the same conditions. On days 1, 30, 60, and 90 the containers are tightly covered, shaken 2 minutes for uniform distribution of mold and then samples withdrawn in stomacher bags and mixed thoroughly with sterile phosphate buffer. Mold counts are obtained using potato dextrose agar as outlined in the Bacteriological Analytical Manual, Food and Drug Administration, 1978. Log mold counts of treated cereal grains, and legume are presented in Table 1. It is obvious from the results that the preservation effect of dimethyl fumarate is far superior to that of calcium propionate.

TABLE 1

| Product | Treatment % DMF | % Calcium Propionate | Log Mold Counts/gm* (Days) 1 | 30 | 60 | 90 |
|---|---|---|---|---|---|---|
| Corn (17% $H_2O$) | 0.3 | — | 2.1 | 2.9 | 3.8 | 4.6 |
|  | — | 0.3 | 1.9 | 4.5 | 6.3 | 8.3 |
|  | 0 | 0 | 2.1 | 5.8 | 7.6 | 8.7 |
| Wheat (15% $H_2O$) | 0.3 | — | 1.6 | 2.2 | 3.4 | 5.1 |
|  | — | 0.3 | 1.8 | 5.2 | 6.8 | 8.4 |
|  | 0 | 0 | 1.9 | 5.9 | 7.2 | 8.9 |
| Milled Rice (14% $H_2O$) | 0.3 | — | 2.2 | 2.1 | 3.2 | 4.1 |
|  | — | 0.3 | 1.9 | 5.2 | 6.7 | 8.2 |
|  | 0 | 0 | 2.1 | 5.8 | 7.4 | 8.6 |
| Soybean (15% $H_2O$) | 0.3 | — | 1.4 | 2.0 | 2.6 | 3.4 |
|  | — | 0.3 | 1.3 | 3.7 | 6.1 | 7.7 |
|  | 0 | 0 | 1.4 | 4.9 | 6.9 | 7.9 |

*A log count of 6/gm usually indicates that the product is unfit for use as human food.

EXAMPLE II

A. Six 5 lb. batches of poultry feed containing 0.2, 0.3 and 0.4% of DMF or calcium propionate are prepared according to the following formula:

| Ingredients | lb/100 lbs |
|---|---|
| Ground yellow corn | 64.5 |
| Soybean meal | 32.0 |
| Bone meal | 2.0 |
| Ground limestone | 1.0 |
| Iodized salt | 0.5 |
| Minor amounts of vitamins | — |

The ground limestone is used as carrier to incorporate appropriate amount of DMF or calcium propionate. Another 5 lb. batch is prepared as a control without adding any preservative. The poultry feed are then kept in seven different plastic bags and maintained at 72° F.±2° F. at a relative humidity of 80–82%. Samples are withdrawn from each bag on day 1, 30, 60 and 90. Mold counts are obtained as described in Example 1. Mold counts of DMF and calcium propionate treated poultry feed are presented in Table 2.

B. Another set of seven 5 lb. batches of poultry feed are prepared and incubated as above except that each batch is deliberately infected by 10 ml water suspension of aflatoxin producing mold, *Aspergillus flavus*. Each milliliter of this suspension contains about $10^6$ molds. They are thoroughly mixed and the infected feed are incubated in a glass chamber at 72° F.±2° F. at a relative humidity of 80–82%. Feed samples from each bag are withdrawn on day 1, 30, 60 and 90 and aflatoxin content analyzed according to the spectrophotometric method of Nabney, J. and Nesbitt, B. F. "Analyst" 90 pp. 155 (1965). Aflatoxin contents of DMF and calcium propionate treated poultry feed are presented in Table 3.

TABLE 2

| Preservative | % by wt. of feed | Log Mold Count/gm (Days) 1 | 30 | 60 | 90 |
|---|---|---|---|---|---|
| Control | 0.0 | 1.7 | 5.2 | 7.4 | 9.1 |

TABLE 2-continued

| Preservative | % by wt. of feed | Log Mold Count/gm (Days) | | | |
|---|---|---|---|---|---|
| | | 1 | 30 | 60 | 90 |
| DMF | 0.2 | 1.9 | 1.8 | 3.3 | 5.8 |
| | 0.3 | 1.7 | 1.8 | 3.1 | 4.5 |
| | 0.4 | 1.9 | 1.6 | 2.4 | 3.6 |
| Calcium propionate | 0.2 | 1.9 | 4.1 | 6.8 | 8.7 |
| | 0.3 | 1.7 | 4.3 | 6.6 | 8.9 |
| | 0.4 | 1.8 | 3.7 | 6.5 | 8.1 |

TABLE 3

| Preservative | % by wt. of feed | Aflatoxin mcg/kg feed (Days) | | | |
|---|---|---|---|---|---|
| | | 1 | 30 | 60 | 90 |
| Control | 0 | 0 | 48 | 615 | 2,376 |
| DMF | 0.2 | 0 | 8 | 36 | 408 |
| | 0.3 | 5 | 10 | 24 | 115 |
| | 0.4 | 0 | 5 | 15 | 85 |
| Calcium propionate | 0.2 | 5 | 42 | 364 | 1,986 |
| | 0.3 | 0 | 26 | 435 | 1,960 |
| | 0.4 | 5 | 32 | 316 | 1,365 |

EXAMPLE III

Ten batches of bread dough are prepared containing 0.25, 0.5, 1.0, 2.0, and 3.0 ounces of DMF or calcium propionate per 100 lbs. of flour. Another batch is prepared as control without adding any preservative. Initially a "sponge" dough is prepared omitting the preservative to facilitate yeast fermentation. Following is the formulation for bread including that of "sponge" and remaining dough.

| Bread Formula | | |
|---|---|---|
| | Sponge (g) | Remaining dough (g) |
| Bread flour | 865 | 465 |
| Water | 457 | 355 |
| Yeast | 33.3 | — |
| Yeast nutrient | 6.6 | — |
| Sugar | — | 106.3 |
| Salt (non-iodized) | — | 26.6 |
| Soybean oil | — | 40.0 |
| Non-fat dry milk solids | — | 80.0 |
| Emulsifier ("Tandem 8") | — | 6.6 |

Emulsifier is used as the carrier of preservatives. Each batch of bread dough is divided into four 18 oz. pieces and following proofing are baked at 410° F. for 20 min. Loaf volume is measured by rapeseed displacement method.

Volumes are found to decrease with increasing level of both DMF and calcium propionate (Table 4). The loaves are then sliced by a slicing machine and individually wrapped in plastic bags. They are then maintained at room temperature (70° F.±2° F.) and observed periodically for visible signs of mold growth. Table 4 provides the data on the loaf volume and mold growth on DMF/calcium propionate containing breads.

TABLE 4

| | Ounces/100 lbs. flour | Volume (c.c.) | Day at which visible mold growth appeared |
|---|---|---|---|
| Control | 0 | 2559 | 12 |
| DMF | 0.25 | 2513 | 25 |
| | 0.50 | 2456 | No visible growth after 475 days |
| | 1.00 | 2396 | — |
| | 2.00 | 2265 | — |
| | 3.00 | 2113 | — |
| Calcium | 0.25 | 2569 | 16 |

TABLE 4-continued

| | Ounces/100 lbs. flour | Volume (c.c.) | Day at which visible mold growth appeared |
|---|---|---|---|
| propionate | 0.50 | 2594 | 16 |
| | 1.00 | 2653 | 18 |
| | 2.00 | 2496 | 22 |
| | 3.00 | 2430 | 28 |

The above results indicate that DMF is a highly effective mold inhibitor for bread. The slight volume lowering effect can be overcome by increasing the proofing time. It should be noted that the DMF-incorporated breads had no sign of ropiness which is usually caused by species of Bacillus.

EXAMPLE IV

Dimethyl fumarate or sorbic acid are applied to oranges, several vegetables and dehydrated fruits using 0.5% solution in isopropyl alcohol. The solutions are uniformly sprayed on the products. Appropriate controls are prepared for each product by spraying with isopropyl alcohol alone. In addition, for comparison there is one batch of each product without any treatment. All the products are kept in open plastic containers. Oranges are maintained at 55° F.±5° F. at a relative humidity of about 90%. Vegetables and dehydrated fruits were held at 72° F.±2° F. at a humidity of 80–82%. All the products are periodically observed for visible signs of mold growth. Table 5 presents the results of DMF/sorbic acid treated oranges, vegetables and dry fruits.

TABLE 5

| Product | % Preservative in spray solution | Day at which visible sign of mold growth appeared |
|---|---|---|
| Orange | No treatment | 6 |
| | Isopropyl alcohol | 7 |
| | 0.5 DMF | 15 |
| | 0.5 Sorbic acid | 9 |
| Onion | No treatment | 5 |
| | Isopropyl alcohol | 5 |
| | 0.5 DMF | 11 |
| | 0.5 Sorbic acid | 6 |
| Potato | No treatment | 6 |
| | Isopropyl alcohol | 6 |
| | 0.5 DMF | 11 |
| | 0.5 Sorbic acid | 8 |
| Yams (sweet potato) | No treatment | 4 |
| | Isopropyl alcohol | 4 |
| | 0.5 DMF | 9 |
| | 0.5 Sorbic acid | 6 |
| Raisin (17% H$_2$O) | No treatment | 30 |
| | Isopropyl alcohol | 33 |
| | 0.5 DMF | 86 |
| | 0.5 Sorbic acid | 47 |
| Prunes (18% H$_2$O) | No treatment | 22 |
| | Isopropyl alcohol | 22 |
| | 0.5 DMF | 97 |
| | 0.5 Sorbic acid | 58 |

EXAMPLE V

An intermediate moisture dog food is prepared using the following formulation.

| Ingredients | (grams) |
|---|---|
| Ground beef | 340 |
| Soy flakes | 330 |
| Sucrose | 160 |
| Corn syrup | 25 |
| Calcium phosphate | 25 |

EXAMPLE IX

In order to demonstrate the application of DMF on food wrappers, three batches of individually wrapped American cheese are treated in the following manner. The wrappers of the first batch (A) are removed and replaced by commercially available plastic wrap (meatwrap). The wrappers of the second batch are replaced by plastic wrap sprayed with isopropanol (B). The wrappers of the third batch are replaced by plastic wrap sprayed with a 0.5% DMF solution in isopropanol (C). The individually wrapped cheese samples are placed in petri dishes and incubated at 55° F.±5° F. at 90% relative humidity. They are periodically observed for visible signs of mold growth. Table 11 presents the days at which mold growth is detected on the cheese samples.

TABLE 11

| Individually wrapped cheese samples | Day at which visible mold growth detected on cheese slice |
|---|---|
| A. Control wrap | 12 |
| B. Wrap sprayed with Isopropanol | 15 |
| C. Wrap sprayed with 0.5% DMF | 21 |

EXAMPLE X

Dimethyl fumarate is mixed at various levels in a commercially produced water-based white paint. Wooden blocks with smooth surface are painted and dried at room temperature. For comparison duplicate blocks are painted with untreated paint. The blocks are then placed in a glass chamber and uniformly sprayed with a suspension of mold obtained from a moldy wooden strip. The painted wooden blocks are maintained at 72° F.±2° F. at a relative humidity of 80–82%. They are periodically observed for visible signs of mold growth. The degree of mold growth is expressed on a 10-point scale where 1 indicates no growth and 10 indicates heavy uniform growth. Table 12 presents degree of mold growth on DMF incorporated paint.

TABLE 12

| Paint Treatment | Mold rating on wooden block (Months) | | | |
|---|---|---|---|---|
| | 1 | 2 | 3 | 4 |
| Control | 1 | 2 | 5 | 8 |
| 0.2% DMF | 1 | 1 | 3 | 4 |
| 0.4% DMF | 1 | 1 | 2 | 4 |
| 0.6% DMF | 1 | 1 | 1 | 3 |
| 0.8% DMF | 1 | 1 | 1 | 1 |

EXAMPLE XI

Three batches of emollient cream are prepared containing (A) no preservative (control), (B) Propyl/Methyl Paraben, and (C) dimethyl fumarate according to the formulations given below. The basic formula is adopted from formula 32 given by Sagarin, E. "Cosmetics Science and Technology," Interscience Publishing, Inc., New York pp. 122, (1957).

| Ingredients | Cream | | |
|---|---|---|---|
| | A (Control) | B (Propyl/Methyl Paraben) | C (DMF) |
| Oil-Soluble Components | | | |
| Light mineral oil | 25.15% | 25.00% | 25.00% |
| Isopropyl myristate | 22.00 | 22.00 | 22.00 |
| Petrolatum | 10.00 | 10.00 | 10.00 |
| Beeswax | 12.00 | 12.00 | 12.00 |
| Paraffin | 5.00 | 5.00 | 5.00 |
| Propyl paraben | 0.00 | 0.15 | 0.00 |
| DMF | 0.00 | 0.00 | 0.20 |
| Water-Soluble Components | | | |
| Water | 25.15 | 25.00 | 25.00 |
| Borax | 0.70 | 0.70 | 0.70 |
| Methyl paraben | 0.00 | 0.15 | 0.00 |
| DMF | 0.00 | 0.00 | 0.10 |

The oil-soluble components and the water-soluble components are measured into two separate large beakers. The beakers are then placed in a water-bath maintained at 75° C. The contents of each beaker are thoroughly mixed with glass rods. The water-soluble mix is then slowly added to the oil-soluble mix with constant, but slow, stirring to form a water-in-oil emulsion. Representative sample from each batch is placed on plastic dishes which are held at 72° F.±2° F. at a relative humidity of 80–82%. They are observed periodically for visible signs of mold growth. Results of mold growth on emollient cream are presented in Table 13.

TABLE 13

| Cream samples (Preservative) | Day at which visible mold growth was detected |
|---|---|
| Control | 32 |
| Propyl/Methyl Paraben | 73 |
| DMF | 96 |

EXAMPLE XII

Spores of Trichophyton are scraped off on a potato dextrose agar plate from an individual with 'Athlete's foot' problem. The plate is incubated for 78 hours at 30° C. Asceptically part of the fungal growth is transferred to a test tube containing sterile distilled water. The test tube is vortexed for 2 minutes and 0.1 ml portions are poured on duplicate potato dextrose plate containing 0.00, 0.001, 0.002, 0.003, 0.004, 0.005% dimethyl fumarate. The inoculum is evenly spread with sterile bent glass rod. The plates are incubated for 48 hours at 30+ C. and the degree of Trichophyton growth expressed on a 10-point scale where 1 indicates no growth and 10 indicates heavy uniform growth. Results of this experiment on the effect of dimethyl fumarate on Trichophyton growth are presented in Table 14.

TABLE 14

| Concentration of Dimethyl Fumarate in Potato Dextrose Agar | Degree of Trichophyton growth |
|---|---|
| 0.000% | 7 |
| 0.001 | 7 |
| 0.002 | 6 |
| 0.003 | 4 |
| 0.004 | 2 |
| 0.005 | 1 |

Dimethyl fumarate completely inhibited Trichophyton growth on Potato Dextrose Agar at a concentration of 0.005%. Since this culture was directly obtained

| Ingredients | (grams) |
|---|---|
| Alphacel | 20 |
| Whey | 15 |
| Salt | 12 |
| Emulsifier (whole egg) | One whole egg |
| Vitamin mix | 1.5 |

The ground beef is thoroughly mixed in a high speed blender with corn syrup and emulsifier. Appropriate amounts of dimethyl fumarate or potassium sorbate are incorporated through corn syrup to give a concentrate of 0.3% based on the total weight of all the ingredients. The remaining ingredients are combined in the above mix using a Kitchenaid mixer. The resulting mass is then heated (pasteurized) on a flat pan to about 200° F. for 15 minutes. Upon cooling the mix is cut into small patties. For comparison a batch is prepared without any preservative. Samples are taken for measuring water activity (Aw) in a Sina-scope hygrometer (Beckman). The water activity ranges from 0.84–0.86 which is quite suitable for mold growth (Cunniff, L. C. "Food Product Development" pp. 76–78, March, 1977). The dog food patties are kept in small ventilated petri dishes held at 72° F.±2° F. at a relative humidity of 80–82%. They are periodically observed for visible sign of mold growth. Table 6 presents the results of DMF/potassium sorbate containing dog food patties.

TABLE 6

| % Preservative in dog food | Day at which visible mold growth detected |
|---|---|
| Control | 4 |
| 0.3% DMF | 18 |
| 0.3% Potassium sorbate | 10 |

EXAMPLE VI

Dimethyl fumarate is applied on various manufactured items and wood chips by uniformly spraying a 0.9% isopropanol solution. To determine the effect of solvent, samples are prepared by spraying isopropanol alone. In addition there is one sample of each which is not treated at all. All of the samples are then held in a glass enclosed chamber at 72° F.±2° F. and at a relative humidity of 80–82%. They are periodically visually observed for fungal growth. The fungal growth is rated on a 10-point scale where 1 indicates no growth and 10 indicates heavy uniform growth. Table 7 presents the results at various stages of observation.

TABLE 7

| Items | Treatment | Fungal rating (Days) | | | |
|---|---|---|---|---|---|
| | | 15 | 30 | 45 | 60 |
| Leather | Control | 2 | 6 | 9 | 10 |
| | Isopropanol | 1 | 6 | 8 | 10 |
| | 0.9% DMF solution | 1 | 1 | 2 | 5 |
| Pieces of pamphlet case | Control | 4 | 8 | 10 | — |
| | Isopropanol | 2 | 8 | 10 | — |
| | 0.9% DMF solution | 1 | 2 | 4 | 6 |
| Canvas pieces | Control | 1 | 4 | 7 | 9 |
| | Isopropanol | 1 | 3 | 6 | 9 |
| | 0.9% DMF solution | 1 | 1 | 1 | 3 |
| Rubber gloves | Control | 1 | 1 | 3 | 5 |
| | Isopropanol | 1 | 1 | 3 | 6 |
| | 0.9% DMF solution | 1 | 1 | 1 | 2 |
| Wood chips (18% H$_2$O) | Control | 1 | 4 | 6 | 8 |
| | Isopropanol | 1 | 4 | 7 | 8 |

TABLE 7-continued

| Items | Treatment | Fungal rating (Days) | | | |
|---|---|---|---|---|---|
| | | 15 | 30 | 45 | 60 |
| | 0.9% DMF solution | 1 | 1 | 2 | 4 |

EXAMPLE VII

Cotton twines are cut into 9" lengths, divided into three batches and then treated as follows. The first batch receives no chemical treatment and thus serves as the control. The second batch is dipped in isopropanol for 5 minutes. The third batch is dipped in 0.9% DMF solution in isopropanol for 5 minutes. All the samples are air dried at room temperature and then uniformly sprayed with a tap water suspension of dirt (soil) to facilitate microbial deterioration. The batches are then packaged in moist plastic bags and stored at 86° F. They are periodically observed for visual signs of mold growth and rated as in Example VI. Table 8 presents the results at various stages of observation.

TABLE 8

| Treatment of Twine | Fungal rating (days) | | |
|---|---|---|---|
| | 10 | 20 | 30 |
| Control | 1 | 3 | 8 |
| Isopropanol | 1 | 3 | 8 |
| 0.9% DMF | 1 | 1 | 4 |

Thus DMF can prevent the biodeterioration of organic fibers that are made into twine, fabrics, sandbags, tents etc. DMF may be incorporated while making the fibers. It may also be incorporated during extrusion of synthetic fibers such as nylon.

EXAMPLE VIII

In a humid basement, on one of the painted walls three 2'×2' areas are marked for this experiment with dimethyl fumate. The 1st square receives no treatment and thus becomes the control. The 2nd square is sprayed with isopropanol and the 3rd square is sprayed with 0.9% DMF solution in isopropanol. At one month intervals, for three months during the summer, the areas are visually observed for fungal growth which is rated on a 10-point scale where 1 indicates no growth and 10 indicates heavy uniform growth. Table 9 presents degree of fungal growth on wall surface treated with dimethyl fumarate. Simultaneously another experiment, with exactly the same procedure is carried out on a bathroom wall covered with wall paper. Fungal growth of wall paper-covered wall is presented in Table 10.

TABLE 9

| Treatment | Fungal rating on wall (months) | | |
|---|---|---|---|
| | 1 | 2 | 3 |
| Control | 2 | 3 | 7 |
| Isopropanol | 1 | 3 | 7 |
| 0.9% DMF solution | 1 | 1 | 3 |

TABLE 10

| Treatment | Fungal rating on wallpaper (months) | | |
|---|---|---|---|
| | 1 | 2 | 3 |
| Control | 2 | 3 | 6 |
| Isopropanol | 2 | 3 | 7 |
| 0.9% DMF solution | 1 | 1 | 3 | from a human subject, dimethyl fumarate is a potential cure for 'Athlete's foot.'

Although the invention has been described in considerable detail with particular reference to certain embodiments thereof, variations and modifications can obviously be effected with the spirit and scope of the invention.

I claim:

1. A process of protecting poultry or animal feed by diminishing the growth of aflatoxin producing mold during the storage of the feed which comprises incorporating in said feed a dialkyl ester of fumaric acid in an amount of at least 0.2% by weight of the feed and wherein the alkyl groups of the dialkyl ester are methyl, ethyl or propyl groups.

* * * * *